United States Patent
Layrolle et al.

(10) Patent No.: US 6,994,883 B2
(45) Date of Patent: Feb. 7, 2006

(54) METHOD FOR APPLYING A BIOACTIVE COATING ON A MEDICAL DEVICE

(75) Inventors: Pierre Jean F. Layrolle, Utrecht (NL); Martin Stigter, Utrecht (NL); Klaas De Groot, Heemstede (NL); Yuelian Liu, Utrecht (NL)

(73) Assignee: IsoTis S.A., Bilthoven (NL)

( * ) Notice: Subject to any disclaimer, the term of this patent is extended or adjusted under 35 U.S.C. 154(b) by 121 days.

(21) Appl. No.: 10/630,340

(22) Filed: Jul. 30, 2003

(65) Prior Publication Data

US 2005/0170070 A1 Aug. 4, 2005

Related U.S. Application Data

(63) Continuation of application No. PCT/NL02/00065, filed on Jan. 29, 2002.

(30) Foreign Application Priority Data

Jan. 30, 2001 (EP) ............................................. 01200329

(51) Int. Cl.
   *A61L 27/00* (2006.01)

(52) U.S. Cl. ...................... 427/2.27; 427/2.1; 427/2.24; 427/2.26; 427/402; 427/403; 427/430.1

(58) Field of Classification Search ................... 427/2.1, 427/2.24, 2.26–2.27, 402–403, 430.1
   See application file for complete search history.

(56) References Cited

U.S. PATENT DOCUMENTS 5,795,750 A     8/1998    Kruse et al. ................. 435/128
6,207,218 B1 * 3/2001    Layrolle et al. ........... 427/2.27

FOREIGN PATENT DOCUMENTS

| EP | 0 806 212 | 11/1997 |
| EP | 0 987 031 | 3/2000 |
| WO | WO 95/13101 | 5/1995 |
| WO | WO 98/41314 | 9/1998 |
| WO | WO-98-41314 | * 9/1998 |
| WO | WO 00/62830 | 10/2000 |

* cited by examiner

Primary Examiner—Jennifer Michener
(74) Attorney, Agent, or Firm—Banner & Witcoff, Ltd.

(57) ABSTRACT

The invention relates to the field of medical devices. More in particular, the invention relates to a method for coating by depositing inorganic ions and a bioactive agent to provide sterile medical devices, wherein said coating improves the biocompatibility and/or bioactivity of a medical device, such as an orthopedic or dental prosthesis. Furthermore, the invention relates to a medical device coated with a method according to the invention and to a reactor for use in a method according to the invention.

12 Claims, 10 Drawing Sheets

Figure 4: Dissolution of biomimetic calcium phosphate coating in saline solution at pH 7.3 at 37°C. Calcium release as function of immersion time.
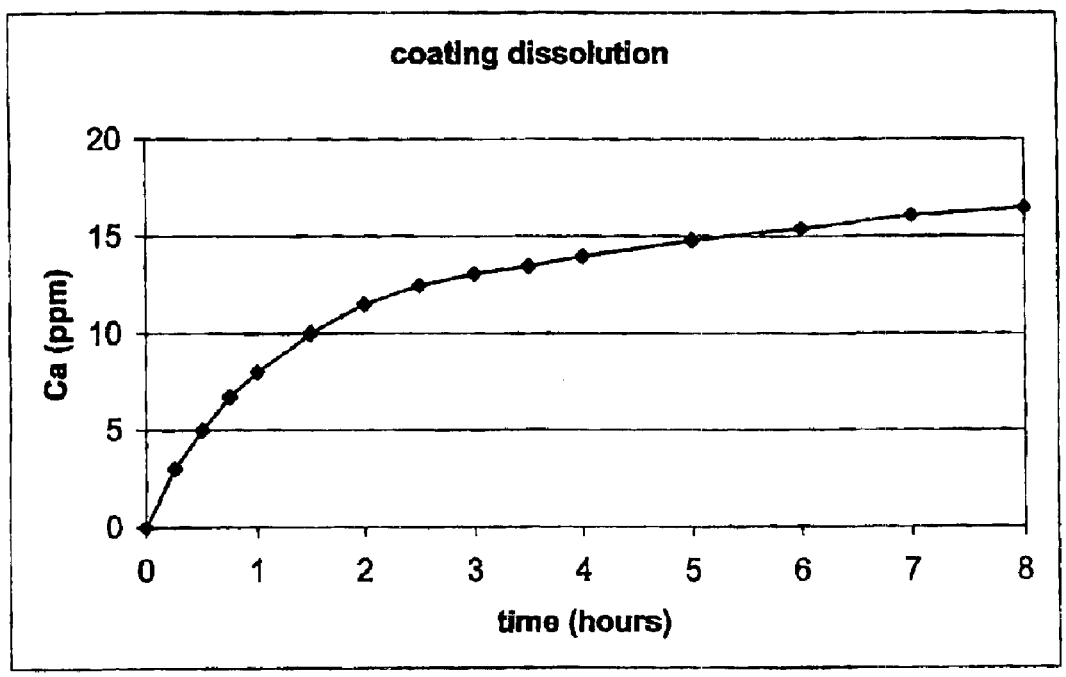

Figure 5: Growth factor release as function of immersion time in saline solution at pH 7.3 and 37°C.
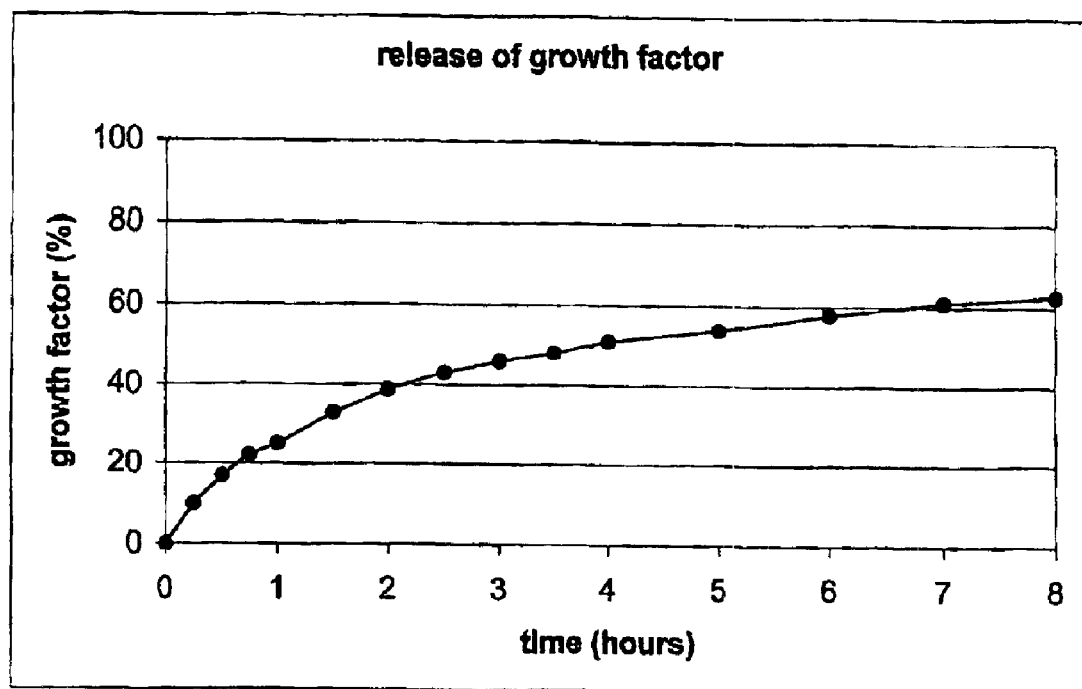

Figure 6: Molecular structure of tobramycin
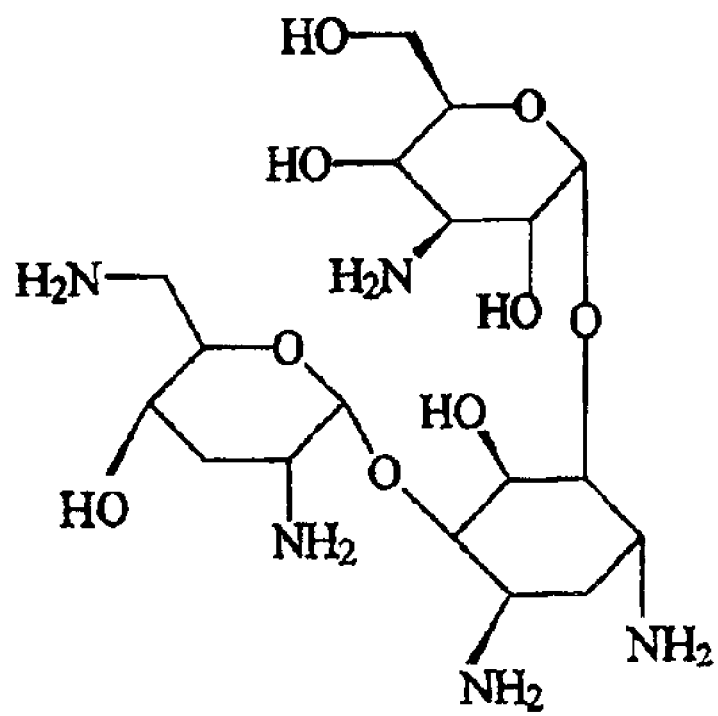

Figure 7: Incorporation of tobramycin in the biomimetic CHA coating by using co-precipitation
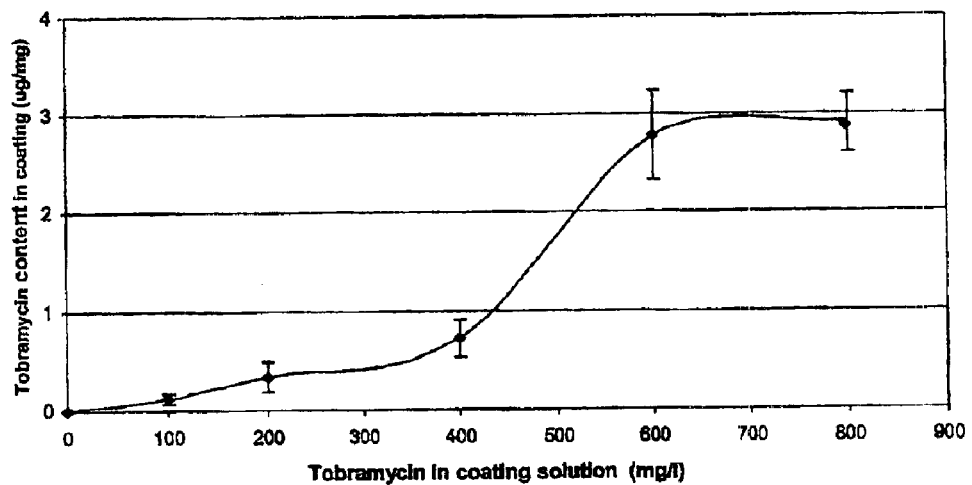

Figure 8: Adsorption of tobramycin on plasma sprayed calcium phosphate coating in different concentrated solution for 10, 40 minutes or 48 hours Figure 9: Inhibition zone for *staphylococcus aureus* bacteria growth observed around a titanium disc coated with the biomimetic CHA coating produced with 250 mg/l tobramycin in solution
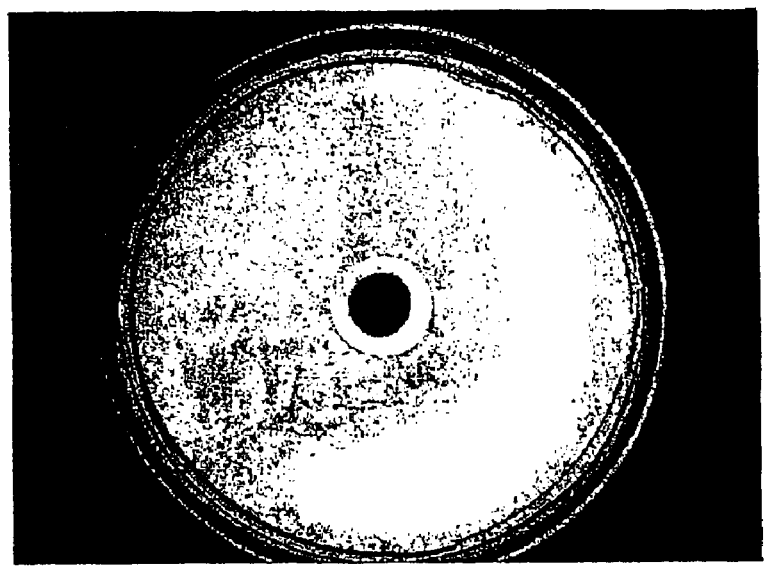

Figure 10: Colony forming units (CFU) per gram of bone around titanium implants coated with apatite coatings without or with tobramycin after injection of 10E6 CFU of staphylococcus aureus in the bone defect an dimplantation for 4 weeks in NZW rabbits.
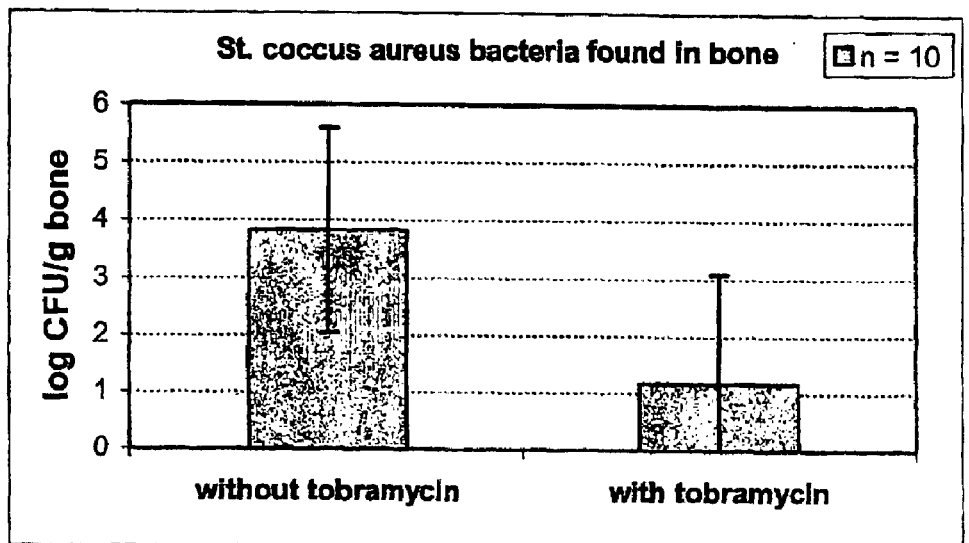

METHOD FOR APPLYING A BIOACTIVE COATING ON A MEDICAL DEVICE

This application is a continuation of International Patent Application Serial No. PCT/NL02/00065, filed on Jan. 29, 2002; which claims priority from European patent application number 01200329.9, filed Jan. 30, 2001; both of which are hereby incorporated herein by reference The invention relates to the field of medical devices. More in particular, the invention relates to a method for coating by depositing inorganic ions and a bioactive agent to provide sterile medical devices, wherein said coating improves the biocompatibility and/or bioactivity of medical devices, such as orthopedic and dental prostheses. Furthermore the invention relates to medical devices coated with methods according to the invention and to reactors for use in methods according to the invention.

Several techniques, such as plasma spraying, flame spraying, electrophoretic deposition, magnetron sputtering and dipping, have been developed for coating hydroxyapatite and other ceramic materials onto medical devices such as implants. The most conventional coating method is plasma spraying.

A drawback of most hydroxyapatite-coated implants is that the anchoring of hydroxyapatite onto the implant requires elevated processing temperatures, which limit the choice of substrate materials and result in high processing costs. In the plasma-spraying process, the raw material i.e. hydroxyapatite, is once molten at a high temperature so that the resulting apatite coatings are different in type from bone apatite. The coatings are frequently thick and brittle and are subjected to fracture at the interface between coating and implant, e.g. between hydroxyapatite and titanium, thereby releasing large particles in the body. Moreover, the method is rather unsuitable for numbers of polymer substrates because of the high temperature involved. Furthermore, it is not possible to incorporate bioactive agents, like proteins or antibiotics, within the coating, which may for example be useful to encourage bone in growth or to prevent infection.

Additionally, most of these coatings are produced in a line of sight process, thereby prohibiting uniform application of hydroxyapatite or other ceramic materials on implants with complex surface geometry (e.g. porous surface). The previous methods have low efficiency for small and round-shaped substrates such as metallic dental implants.

Recently, a biomimetic coating has been developed for coating a medical implant with ceramic materials, such as bone-like hydroxyapatite. This technology has been disclosed in European patent application 98203085.0 and comprises soaking an implant material, e.g. a scaffold for tissue engineering bone, into a super saturated calcium phosphate solution resembling a physiological fluid. A calcium phosphate layer uniformly precipitates on the implant surface under modulated nucleation and crystal growth conditions. This method mimics the way hydroxyapatite bone crystals are formed in the body. Considering the physiological conditions under which the biomimetic coating is grown from a fluid at body temperature, bioactive agents, such as (bone) growth factors, antibiotics, can be co-precipitated.

Many mineralized tissues in living organisms are composed of crystals formed under well-controlled conditions. Among the group of bioactive agents, peptides, polypeptides and proteins are key participants in the control process. Some of these, in particular some proteins, envelop the individual crystals, whereas others are occluded inside the crystals. How occlusion inside a crystal takes place and what the role of peptides, oligopeptides, polypeptides and proteins is in the crystallization process and in the determination of the properties of the crystal still remains unclear.

Recently coating methods for medical implants have been developed in which proteins are incorporated during deposition of a calcium phosphate on implants. Since many bioactive agents are expensive drugs, it is important to be able to conduct the coating process in a small volume with a relatively high concentration of those agents in order to reduce the minimum required amount of these compounds in the coating process. On the other hand, in order to obtain a ceramic layer of sufficient thickness it may be required to use a large volume of coating solution, in which the bioactive agent which is to be incorporated, is present. Normally devices for medical use are sterilized in order to avoid the chance that toxic or pathogenic micro-organisms on or in a medical device may infect subjects that are treated with a medical device. However, since many bioactive agents, including proteins and other peptidic compounds cannot be treated by high temperature sterilization or by sterilization with high doses of radiation, without changing their chemical or physical structure, a method to coat medical devices with a coating comprising those bioactive agents should be a sterile or aseptic process.

The present invention seeks to find a way of providing a medical device, such as an implant, with a coating of a ceramic material (i.e. a material formed in the presence of inorganic ions such as calcium and phosphate), wherein said coating further comprises a bioactive agent, and optionally one or more other compounds. It is an important object of the invention to provide a method wherein a minimal amount of bioactive agent is required in a method to apply a coating with a certain amount of said bioactive agent on a medical device. Preferably such a process should take place under sterile conditions in order to avoid the introduction of potentially hazardous compounds or organisms into the coated medical device. Thus sterilization after coating can be avoided, which is beneficial since (a large portion of) a bioactive agent is likely to lose its activity due to a sterilization process.

These objects, as well as other objects of the invention that will become clear from the present description, have been achieved by virtue of applying a coating by depositing inorganic ions and one or more bioactive agents, e.g. growth hormones, vitamins, cell adhesion factors, the tri-peptide arginine-glycine-aspartic acid (RGD), fibrin, fibronectin, antibiotics, and/or proteins, peptides, oligopeptides, or polypeptides in general, on medical devices in a specific manner.

BRIEF DESCRIPTION OF THE DRAWINGS

FIG. 4 graphically depicts dissolution of a biomimetic calcium phosphate coating in. saline solution at pH 7.3 at 37° C.

FIG. 5 graphically depicts growth factor release as a function of immersion ime in saline solution at pH 7.3 and 37° C.

FIG. 6 depicts the molecular structure of tobramycin.

FIG. 7 graphically depicts incorporation of tobramycin in a biomimetic CHA coating generated by co-precipitation.

FIG. 8 graphically depicts adsorption of tobramycin on a plasma-sprayed calcium phosphate coating.

FIG. 9 depicts the zone of inhibition observed for *Staphylococcus aureus* growth around a titanium disc coated with a biomimetic CHA coating containing tobramycin.

FIG. 10 graphically depicts colony forming units (CFU) per gram of bone observed around titanium implants coated with apatite in the presence or absence of tobramycin after injection of $10^6$ CFU of *Staphylococcus aureus* in a bone defect.

Figure 1:
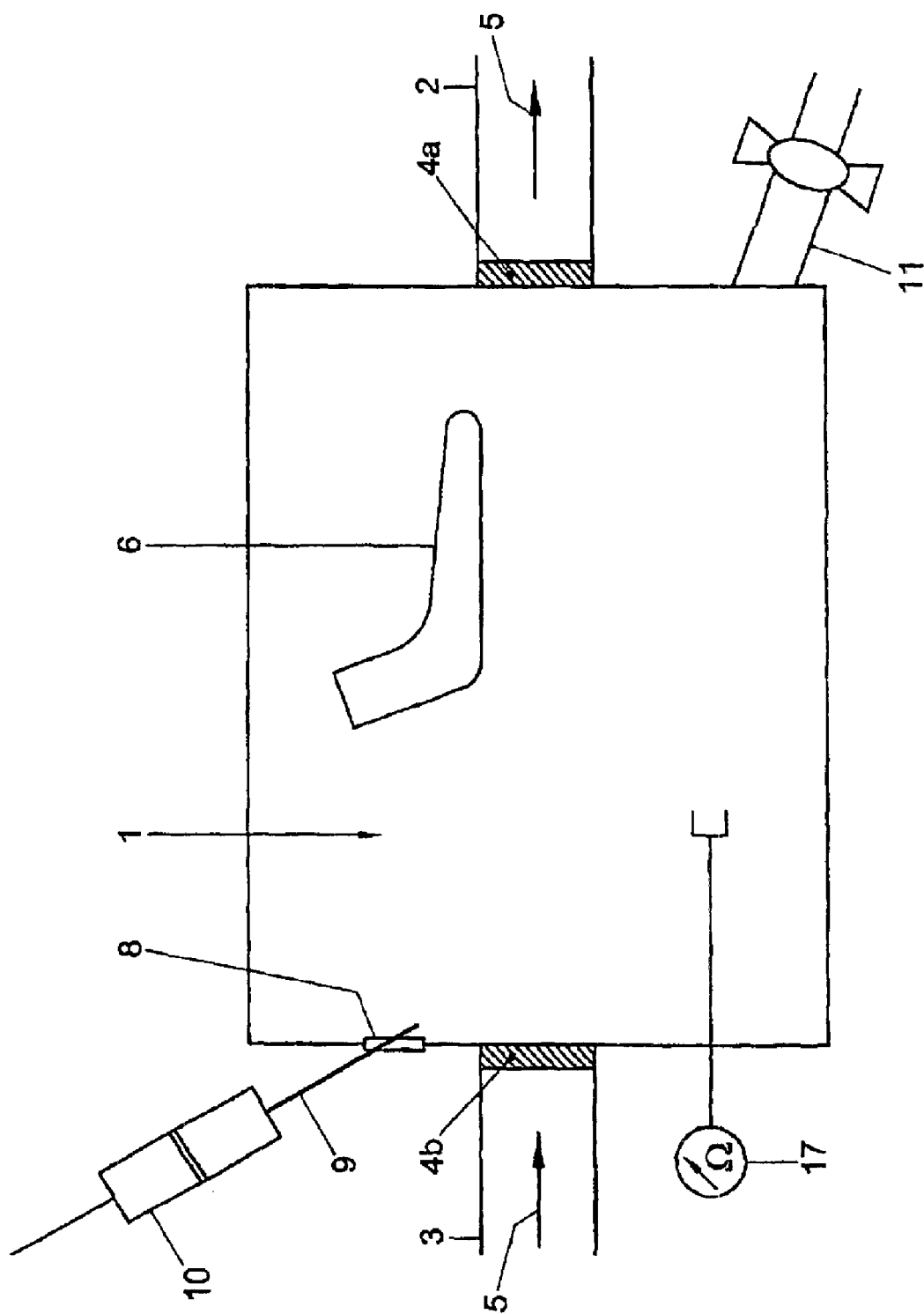
FIG. 1 depicts a schematic illustration of a basic reactor.

Surprisingly it has been found possible to coat a medical device under aseptic conditions with a layer of an inorganic material and one or more bioactive agents, by bringing the device into contact with a coating solution in a reactor, wherein this reactor has been specifically designed so that a coating solution in the reactor can pass through the reactor, whilst the bioactive agents are retained inside the reactor e.g. by one or more partitions. The amount of bioactive agent required to incorporate a certain amount of said bioactive agent into a coating on a medical device, can thus be very low.

Accordingly, the invention relates specifically to a method for coating a medical device comprising depositing inorganic ions and a bioactive agent on the device in a reactor, wherein inorganic ions are deposited from a stream of a coating solution passing through said reactor, which reactor is provided with at least one partition to retain the bioactive agent in the reactor.

The present invention also relates to a reactor for use in said method and to a medical device comprising a coating obtained by a method according to the invention.

The terms Aseptic or sterile refer to a condition essentially free of factors that may cause putrefaction or infection. Such hazardous factors include organisms, e.g. toxic or pathogenic bacteria, fungi, anti-gens and parasites, and other potentially hazardous moieties, e.g. viruses and prions.

The term bioactive agent, as used herein refers to an agent capable of inducing or affecting an action in a biological system, e.g. by inducing or affecting a therapeutic or prophylactic effect, an immune response, tissue growth, cell growth, cell differentiation or cell proliferation.

Compounds that contain peptide-bonds such as peptides, oligopeptides, polypeptides and proteins will generally be referred to as peptidic compounds, regardless of the number of amino acid residues they are formed of.

The term partition as used herein, refers to a structural element or a provision by which two or more parts, i.e. inorganic ions and one or more bioactive agents, can be separated. Examples of partitions are semi-permeable membranes, ion selective membranes, molecular weight cut-off filters and apparatus to separate inorganic ions and one or more bioactive agents from each other.

A coating according to the invention may be applied to any medical device, made of inorganic, metallic or organic materials. Metallic, organic, polymeric and ceramic medical implants form a particularly suitable group of medical devices in relation to the present invention. The medical device may be flat, dense or of a complex shape. It may have a porous, beaded or meshed ingrowth surface.

Metals comprising stainless steel, titanium and alloys thereof, such as nickel/cobalt, cobalt/chrome alloys and tantalum, can be coated by depositing inorganic ions for orthopaedic and dental applications. For example, implants used in total hip arthroplasty such as porous or non-porous acetabular cups and the proximal region of hip stems may be coated by depositing bioactive agents and inorganic ions, such as calcium and phosphate.

Ceramic materials comprising alumina and zirconia, glasses such as bioactive glasses made of $CaO\text{-}SiO_2\text{-}P_2O_5$ or ceramics like hydroxyapatite or β tricalciumphosphate (TCP) may be coated with the bioactive carbonated calcium phosphate layers, also comprising bioactive agents such as growth factors.

The subject coatings can be applied to various polymers and plastics, more preferably biocompatible or bioresorbable ones like polyactive™.

Before applying the coating, the substrates are preferably cleaned or treated to remove any surface contaminants and to promote good adhesion of the coating. Various methods for cleaning may be employed. Metallic medical devices may be rinsed with a degreaser, i.e. acetone, alkyl alcohols, etc. and then thoroughly rinsed with pure water.

In order to improve coating adhesion, various surface treatments may be applied to metal implants. Preferably medical devices are treated to obtain a roughness with an Ra of at least 3 µm, prior to coating the device according to a method of the present invention, if it does not already have a desired roughness, as is described in the European patent application 97201424.5. Mechanical surface treatments, such as sand-blasting, scoring, polishing and grinding can increase surface roughness of the implants and improve the bonding strength between the coatings and metal substrate.

For similar purposes, chemical surface treatments may be also applied to metal substrates prior to coating. Among others chemical treatments available for metals, acid etchings will be preferred by treating implantable devices with strong mineral acids, such as hydrofluoric, hydrochloric, sulfuric, nitric and perchloric acids. It may also useful to treat the metal devices with oxidizing agents such as nitric acid, peroxyhalogen acids, hydroxyperoxides, or hydrogen peroxide to form a fresh metal oxide layer. After the mechanical or chemical treatment, it is necessary to rinse the medical devices with pure water under ultrasounds for removal of surface contaminants.

Prior to applying the coating, the equipment used and the medical device to be coated are preferably be sterilized e.g. by autoclaving under water steam. A typical sterilization procedure consists of autoclaving the equipment and medical device in a steam at 100–130° C. for 30 minutes.

Prior to coating the medical device with a layer of an inorganic compound and a bioactive agent it is highly preferred to "pre-coat" the medical device with a initial layer (pre-coat) of inorganic compounds, such as with an initial layer comprising calcium and phosphate. A highly suitable method for applying a pre-coat according to this embodiment is disclosed in European Patent Application 98203085.0. Said pre-coat is most preferably obtained under high nucleation rate to obtain a thin and amorphous calcium phosphate layer. It is not necessary to produce the pre-coat aseptically, because a pre-coated medical device may be sterilized by steam prior to applying a coating comprising a bioactive agent. The provision of a pre-coat has been found particularly advantageous when the medical device is a bone substitute. The pre-coat can advantageously act as a seed surface for a coating, to be applied in accordance with the invention. In principle a coating applied in a method according to the invention, can be deposited on a medical device with or without a pre-coat as mentioned above. It has been found that, among other factors, the stability and the activity of the coating comprising a bioactive agent is significantly enhanced when it has been deposited on a medical device with a pre-coat such as described above.

The device, whether it has been pre-coated or not, may be sterilized such as mentioned above prior to applying a coating in a method according to the invention. The coating method described herein is used to deposit inorganic ions and one or more bioactive agents under aseptic conditions on the surface of a medical device. The bioactive agent co-precipitates together with inorganic ions, which form a crystalline coating. The resulting coating is accordingly a ceramic coating with the one or more bioactive agents incorporated therein. For the coating, the use of inorganic ions selected from the group of calcium ions, magnesium ions, sodium ions, phosphate ions, carbonate ions, chloride ions and hydroxide ions are particularly preferred. Phosphate is defined herein as any inorganic phosphate, including $PO_4^{3-}$, $HPO_4^{2-}$, $H_2PO_4^-$; carbonate is defined herein as any inorganic carbonate, including $CO_3^{2-}$ and $HCO_3^-$.

In a particularly preferred embodiment of the invention, the inorganic ions form a coating of a calcium phosphate compound, in which the bioactive agent is incorporated. More preferably the coating further comprises carbonate and/or other ions on the surface of a medical device. The inorganic component of the coating may e.g. be amorphous carbonate calcium phosphate, hydroxyapatite, calcium deficient and hydroxyl carbonate apatite, octacalcium phosphate, dicalcium phosphate dihydrate, calcium carbonate or a combination thereof. The inorganic component of the coating may be similar in composition and crystallinity with bone and teeth minerals and may have desired bioresorbability and/or bone-bonding properties to improve the biological fixation of medical implants to living calcified tissue.

A wide variety of bioactive agents may be incorporated by employing a method according to the invention. Preferred bioactive agents include peptides and proteins such as growth factors, e.g. Bone Morphogenetic Proteins (BMP), epidermal growth factors, e.g. Epidermal Growth Factor (EGF), fibroblast growth factors, e.g. basic Fibroblast Growth Factor (bFGF), Nerve Growth Factor (NGF), Bone Derived Growth Factor (BDGF), transforming growth factors, e.g. Transforming Growth Factorβ (TGF-β), Transforming Growth Factor-β1 (TGFβ1), human Growth Hormone (hGH) vascular growth factor, and combinations thereof.

Autologous serum, which is essentially a mixture of bioactive agents, may be co-precipitated in a coating according to the invention together with or instead of one or more other bioactive agents. Autologous serum maybe obtained from the patient, into whom the medical device may be implanted. Methods to obtain said serum are known from the art. It can for example be obtained from the plasma fraction of centrifuged blood. Particularly preferred are bone growth factors, including BMP, which is capable to stimulate bone growth. It is possible to incorporate bioactive agents that enable the coating to serve as drug delivery system. For example, the gradual release of growth factors, around the coated device can stimulate osteoblasts cells and enhance bone healing.

Other examples of bioactive agents that can be incorporated into a coating are growth hormones, e.g. dexamethasone, vitamins, e.g. vitamin D3, antibiotics like gentamycin, tobramycin, vancomycin, antimicrobial agents, e.g. penicillins, cephalosporins, aminoglycosides, macrolides, tetracyclines, anti-inflammatory agents, antiviral agents, hormones and hormone antagonistics, centrally acting (opoid) analgesics, local anesthetics chemotherapeutic agents, e.g. sulfonamides, urinary tract antiseptic drugs for tuberculosis, drugs for leprosy, anti-tumor agents, chemotherapy of amebiasis, anti-malarial agents, anti-helminthiasis agents, anti-gout agents, drugs for Parkinson's disease, centrally active muscle relaxants, corticosteroids, e.g. mineralocorticosteroids, glucocorticosteroids, androgens, e.g. androgenic steroids used in therapy, anabolic steroids used in therapy, antiandrogens, estrogens, estrogenic steroids used in therapy, anti-estrogens, progestins, thyroid drugs e.g. thyroid drugs used in therapy and antithyroid drugs used in therapy, and the like. In particular for a coating on a bone substitute, dexamethasone and/or vitamin D3, are particularly preferred examples of non-peptidic and non-proteinaceous bioactive agents that can be incorporated into a coating according to the invention.

Generally, the incorporated bioactive agents will be solubilized in solvent comprising compounds that are also present in the coating solution, more preferably this solvent has the same composition as the coating solution. In case a buffer is used in the coating solution that does not (easily) permeate through the partition to retain the bioactive agent (see description of the reactor below), buffer should also be dissolved in the solution comprising the bioactive agent. Typically the concentration of the one or more bioactive agents in the solution will be in a concentration range of 0.1 mg/l to 10 g/l, preferably, 0.1–1000 mg/l, more preferably 0.1–500 mg/l, most preferably 0.1–20 mg/l. Depending upon the desired type of coating the skilled professional may choose to use particular concentrations, pH ranges and temperatures to carry out a method according to the invention. Most preferably calcium and phosphate are among the inorganic ions used to coat a medical device by depositing inorganic ions and bioactive agents in a method according to the invention. A coating solution for depositing calcium and phosphate ions (i.e. a calcifying solution), is preferably buffered at a pH in the range of 6 to 8.

The selected pH may depend upon the isoelectric point (pI) of a bioactive agent that is to be incorporated into the coating. Co-precipitation of bioactive agent with inorganic crystals is related to electrostatic interactions. For chargeable compounds, and in particular for amphoteric compounds, the efficiency of incorporation depends on pI of the bioactive agent and pH of the coating solution. The pI of a compound can be measured by isoelectric foccussing e.g. on a gel. Preferably the bioactive agent is charged at the pH at which the device is coated according to the invention., because this positively affects the amount of bioactive agent that is incorporated.

For instance, BMP-2 has a IEP of 9.2. Accordingly the protein has a positive charge below 9.2 and negative charge above 9.2. At a pH of 7.4 for the coating solution, the protein is positively charged and thereby interacts with anions (such as phosphate) in solution, which enhances co-precipitation with crystals (e.g. apetite crystals) growing on the implant surface. For instance, a concentration of BMP-2 in a coating solution of 5 mg/L may lead to an incorporation of 5 $\mu$g/mg of coating at pH 7.4. BMP-7, however, has an IEP of 7.7. At a pH of 7.4, the efficiency for incorporation is low due to insufficient difference between IEP and coating pH. Under the same conditions, the incorporation of BMP-7 is only 0.25 $\mu$g/mg coating at pH 7.4 for 5 mg/l of BMP-7 in coating solution. In order to increase efficiency of incorporation, a lower pH for coating solution should be selected (e.g. 6.7). In a preferred embodiment the difference between pH and pI is at least about 1 pH unit for optimal co-precipitation of bioactive agent with the growing inorganic layer. For basic amphoteric compounds (pI>7.0) coating is preferably performed at a pH below pI, for acidic amphoteric compound (pI<7.0) coating is preferably performed at a pH higher than pI. For compounds with a pI of 7.0 a pH close to 6 or close to 8 is preferred. In case several compounds with different pI's are to be incorporated, it is preferred to choose a pH, where all bioactive agents are charged, if possible.

For uncharged bio-active agents the pH of the coating-solution has less influence on the incorporation rate, may be. In general physiological pH, around 7.4 is very suitable. An appropriate buffer, like tris(amino-ethane) or HEPES (N-[2-hydroxyethyl]piperazine-N'-[4-ethanesulfonic acid]) is preferably used to maintain the desired pH. Suitable buffers to maintain a desired pH are known from the art. Such buffers preferably have a $pK_a \pm 0.5$ around the desired pH. These buffers are preferably present in a concentration between 10 and 100 mM/l and adjusted to the correct pH with hydrochloric acid or sodiumhydroxide.

The concentration of calcium ions in the coating solution may range from 0.5 to 10 mM, more preferably from 0.5 to 5 mM. The concentration of phosphate may range from 0.5 to 6 mM, more preferably from 0.5 to 3 mM. The concentrations of calcium and phosphate may have to be adjusted to the pH in order to maintain supersaturation. The solubility of calcium phosphate increases with a decrease in pH. At 37° C., at a pH of 6.7 calcium phosphate is more soluble than at physiological and thereby concentrations of calcium and phosphate should be within or 4–10 mM and 2–20 mM, respectively.

The relation between temperature, pH and calcium phosphate solubility per se is known from the art. The skilled professional will be able to derive suitable conditions from the values mentioned above. Information on solubility calculations can also be found in "G. Vereecke & J. Lemaître: Calculation of the solubility diagrams in the system $Ca(OH)_2$-$H_3PO_4$-$KOH$-$HNO_3$-$CO_2$-$H_2O$, J. Crystal growth 104 (1990) 820–832. Furthermore the presence of magnesium ions in the coating solution is thought to be essential to allow deposition of a crystalline coating. Particularly, the presence of magnesium has been found to be important for controlling the crystal growth of the coating during deposition from the coating solution. An optimum control of crystal growth leads to a uniform, strong and wear resistant coating. Particularly, the attachment of the coating to the substrate is beneficially affected by the presence of magnesium ions in the coating solution. Magnesium and carbonate ions are preferably present in concentrations below 1 and 5 mM, respectively. The quantity of Mg and $HCO_3$, both inhibitors of crystal growth may be adjusted for optimal attachment of coating. In the case of apatite, apatite crystals (>10 microns) are usually poorly attached to a surface of a medical devices. while submicrometer crystals (<1 microns) lead to a mechanically stronger coating. The average size of the crystals can be decreased by increasing the magnesium and carbonate concentration.

Sodium chloride, or any suitable salt may be added to maintain the ionic strength of the coating solution at a value of 0.05 to 0.5 mM, preferably 0.1 to 0.2 mM.

The composition and crystal size of the layers will be strongly dependent on the amount of crystal growth inhibitors in the coating solutions.

Particularly when applying a coating comprising calcium phosphate on a medical implant, the ions and bioactive agent will typically be allowed to deposit until a layer has been formed on the medical devices of about 0.5 to about 100 microns, preferably of about 25 to about 50 microns.

Particular good results have been achieved with a medical device for use as a bone substitute that has initially been pre-coated with a thin amorphous layer of calcium phosphate (as described herein) and subsequently has been coated with a hydroxyapatite, comprising one or more growth factors and optionally on or more other bioactive agents. It has been found that due to the presence of a growth factor in the coating, cell activity and cell differentiation is stimulated near implanted medical devices according to the invention to regenerate bone tissue more efficiently and more rapidly than near implanted medical which do not contain said growth factor. The release of bioactive agent(s) is related to the coating degradation. After implantation the mineral coating is remodeled or degraded by osteoclastic activity, leading to a gradual release of the bioactive agent(s), around the implanted medical device. Thus an optimal concentration of bioactive agent(s) can be maintained around the medical device, and burst-release of bioactive agent(s), which may lead to unwanted side effects, is avoided.

In vitro, the degradation of the coating can be monitored by measuring the calcium release under physiological conditions as a function of the time. Methods to monitor calcium are known from the art and include monitoring via a calcium-ion selective electrode. It has been found that at physiological pH (7.4) a bioactive agent such as a growth factor is released at the same rate as calcium.

As has been mentioned, an important feature of the invention is the use of a reactor which is specifically designed to allow a stream of coating solution to pass through it and to retain the bioactive agent inside. A reactor according to the invention will be described in more detail below with reference the attached Figures. This description and the Figures should not be construed as to limit the invention. As will be understood by the skilled person, many variations are possible without leaving the scope of the invention.

A schematic illustration of a basic suitable reactor is shown in FIG. 1. The reactor comprises a reactor vessel (1) which is preferably made of an inert and autoclavable material, preferably a material like polycarbonate, borosilicate glass or stainless steel coated with Teflon™ to avoid deposition or encrustation of carbonated calcium phosphate on the inner side walls. Depending upon the size of the medical device (6) and the number of these devices that are to be placed together inside the reactor, the volume of the reactor vessel will typically vary from 0.1 to 10 l preferably from 0.5 to 2 l. The reactor vessel volume may further be optimized depending upon the desired amount of bioactive agent that is to be incorporated into the coating.

The reactor vessel preferably has a sealable opening (not shown) large enough to place a medical device (6) inside the reactor vessel, such as a removable top-half of the reactor vessel, a closable hole in the reactor vessel wall and the like, an inlet (3) and an outlet (2) for coating solution. The inlet and outlet for coating solution can be situated at any side of the reactor. Inlet and outlet preferably comprise quick fit connections. It is preferred to have inlet and outlet on opposite sides, e.g. one at the left, the other at the right or one at the bottom the other at the top. In a preferred embodiment selective retention is achieved by equipping the reactor vessel at the outlet side and, optionally, a the inlet side with one or more partitions (4a and 4b) that are permeable towards inorganic ions in the coating solution (5) but especially not towards a bioactive agent inside the reactor vessel (1) that is to be incorporated in the coating on the medical device (6). Most preferably the inlet comprises a filter (e.g. a 0.2 micron filter), which prevents contamination from entering the reactor vessel. Thus the filter helps to maintain sterile conditions.

A particularly suitable type of partition is a membrane such as a molecular weight cut-off membrane, i.e. a membrane that is permeable to ions and molecules up to a particular size. The cut-off membrane will be chosen to have a pore-size small enough to retain the (smallest) bioactive agent that should be held inside the reactor vessel for incorporation into a coating on a medical device. Such a membrane is particularly useful when polymers, such as peptidic compounds with a molecular weight of at least 10,000 g/mol, are to be incorporated. Of course it is also possible to use membranes with a lower molecular weight cut-off in case smaller compounds are to be retained or to use membranes with a higher-cut off. In case the compounds that are to be incorporated are proteins, such membranes may be known as low protein binding membranes. For bioactive compounds with a molecular weight of 30–70 kDa, particularly preferred partitions are filters with a molecular weight cut-off of 10 kDa. Such filters can be obtained from various sources. Particular preferred partitions are filters for tangential flow filtration (TFF) or cross-filters.

In TFF, a fluid is pumped tangentially along the surface of a membrane. A stream will be generated by pumping solution from the reactor to the filter (feed stream). The flow of the filtrate stream (comprising the inorganic ions and substantially no bioactive agent) can be regulated with the feed pressure and retentate pressure (retentate comprises the bioactive agent).

Optionally the retentate may be mixed with the stream leaving the reactor to regenerate the bioactive agent from the bulk solution by concentrating the bioactive agent in the stream leaving the reactor. The retentate may be mixed with the coating solution and be pumped back into the reactor-vessel.

The use of a double-jacketed reactor vessel helps to maintain a constant temperature in the reactor vessel. In a preferred embodiment the temperature in the reactor vessel can be controlled by a system for heating and/or cooling, e.g. by a thermocouple linked to a thermo-circulator capable of cooling and heating to maintain the desired temperature, or by other means that are known from the state of the art (not shown in drawing).

In some embodiments of the invention, medical devices, e.g. hip stems, dental implants or acetabular cups, can be held in the reactor vessel by special hooks fixed on the head-plate of the reactor vessel. Accessories mounted to the head-plates of the reactor vessel are usually isolated with o-ring joints and filters to maintain sterility during the coating process.

The reactor vessel may also comprise a stirring system, such as a magnetically coupled stirring system, or another stirring system known in the art.

The reactor may further comprise a provision for adding bioactive agents to the reactor vessel. This can for example be an aperture (8) in the top of the reactor vessel, sealable with a screw-cap and/or a septum through which a needle (9) can be stuck, wherein said needle may be attached to a syringe (10) or another container for bioactive agents that can thus be introduced into the reactor vessel. It is also possible to use a valve to open and close the aperture and add the bioactive agent. Preferably a bioactive agent is added aseptically, e.g. via injection through the septum mentioned earlier, prior to starting the flow of coating solution through the reactor vessel. The reactor may further comprise a drain (11) to dispose of the liquid contents and/or small particles inside the reactor. Optionally a sterilizable combined glass electrode is present in the reactor to monitor the pH of coating solution as a function of time during the reaction. Also other sterilizable ion-selective electrodes may be present to monitor the concentration of such ions during the process.

A reactor vessel may also comprise an instrument (17) to measure the variation of the thickness of the coating in time. For this purpose, a novel conductivity cell may be used comprising two conductive plates between which the conductivity or resistance is measured during the coating process. During the coating process a layer of bioactive coating will also gradually be deposited on the metal plates. As a result the resistance will increase and the conductivity will drop, thus indicating the change in thickness of the coating. In case the medical device is made of a conductive material, the electrodes are preferably made of the same material as the medical device. In general, metal electrodes, e.g. made of platinum or another inert metal, are very suitable. Preferably the electrodes are placed in parallel.

Naturally this conductivity cell can also be used during a redissolving process of the inorganic part of the coating.

In another embodiment, particularly if the reactor is also used to deposit a pre-coat (as described above), the reactor may comprise an inlet to provide a gas into the reactor vessel. Such an inlet may also be used to agitate the solution inside the reactor vessel. The introduction of a gas can be achieved by a gas-inlet pipe and a porous sparger for producing tiny gas bubbles (e.g. $CO_2$) into the solution inside the reactor vessel and thus increases the gas exchange surface or aeration of the coating solution. An electro-valve or solenoid valve controls the flow of gas introduced into the reactor vessel. Particularly in an embodiment wherein it should be possible to alter the gas source, valves such as electro-valves or solenoid valves may also be used for selection of the gas that should flow through the reactor. The flow of gas can be regulated as a function of time or pH, if a pH meter is present somewhere in the coating device.

Furthermore, in an embodiment of the invention comprising bubbling with a gas in the reactor vessel, said reactor vessel preferably has an aperture to avoid increasing the internal pressure and to allow the natural release of gas out of the coating solution. In order to maintain aseptic conditions, a filter (e.g. a 0.2 microns filter) may be present at the inlet and the outlet for the gas. Particularly in case an outlet for gasses is present, the head-plate of the reactor vessel is preferably equipped with an outlet condenser to prevent evaporation of coating solution. In some embodiments of the present invention, an inert gas may be led through the reactor vessel to dry the medical device via the construction described above. In a preferred embodiment, the reactor vessel is a cartridge-like structure wherein partitions for retaining the bioactive agents can be held and replaced. Optionally, the cartridge structure may provide the sealable opening for placing medical devices inside the reactor vessel.

A reactor according to the invention may be connected to one or more other devices. A schematic representation of a possible set-up is shown in FIG. 2.

Figure 2:
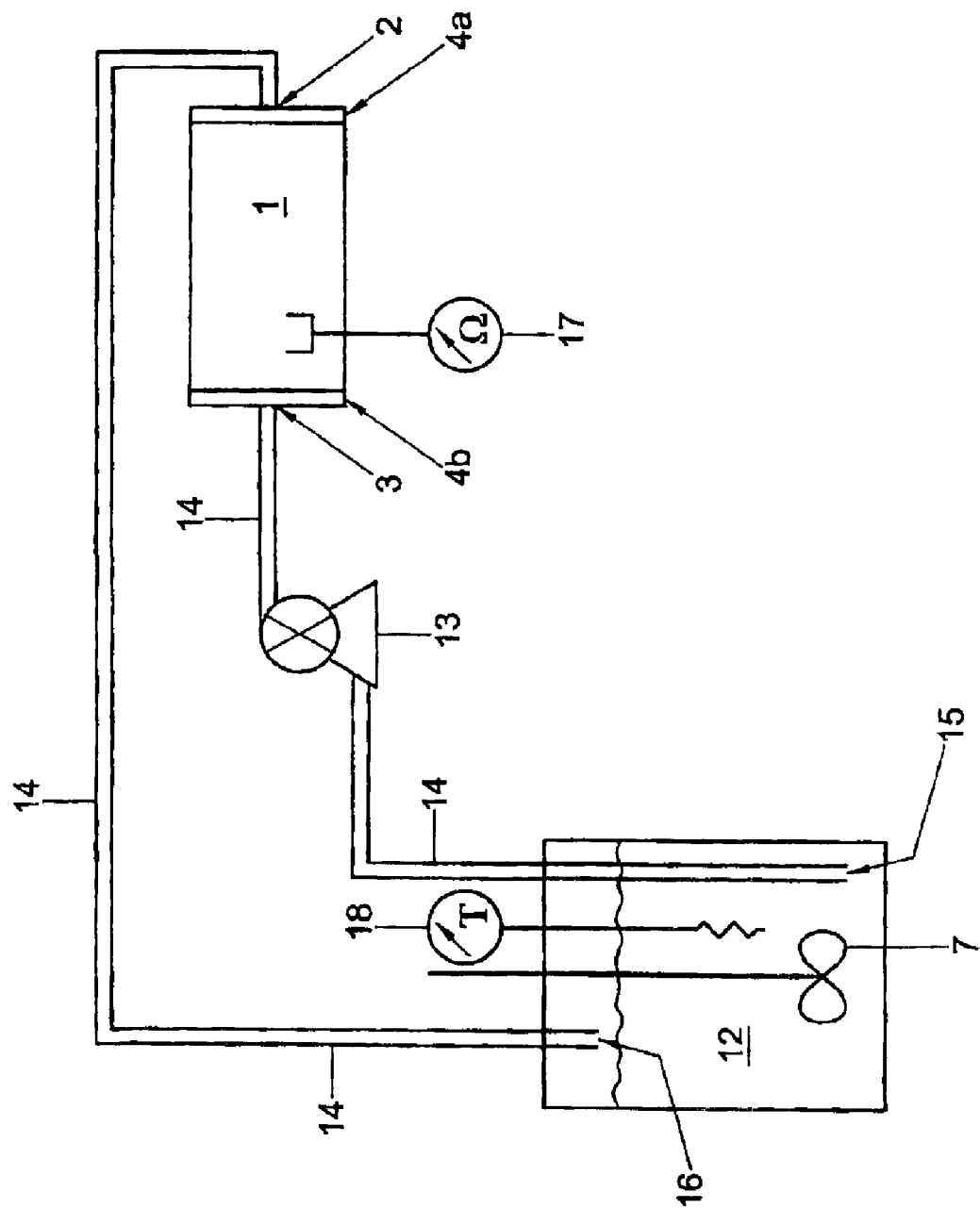
FIG. 2 depicts a schematic illustration of a reactor for coating a medical device.

In FIG. 2, a reactor for coating a medical device according to the invention further comprises a container for coating solution (12) which is connected to a reactor vessel (1) and a pump (13) for transporting coating solution from said container via an inlet (3) for coating solution through said reactor vessel.

In a preferred embodiment the reactor vessel is furthermore connected to said container via the outlet (2) for coating solution of said reactor vessel. Thus coating solution can continuously or intermittently flow from the container for coating solution via the reactor vessel back to said container. This flow process is called recirculation, which allows for a reduction of the required amount of coating solution.

The connections (14) between container(s), pump(s) and reactor vessel(s) are typically closed channels, e.g. tubes or pipes made of inert material, such as peek, silicon, stainless steel, preferably coated with teflon, or another material to which protein has a low binding affinity. The internal diameters of these channels are typically chosen to be wide enough, to prevent clogging by precipitated salts. The internal diameter of the channels will typically be in the range of 0.1 to 10 mm, although it is possible with in the scope of the present invention to use more narrow or wider channels.

Any type of pump to create the flow of the solutions through the set-up may be used, as long as it can provide a large enough flow of solution and does not put maintaining aseptic conditions at risk. The required flow may vary widely depending upon the coating requirements and the surface size of the medical device. Without being limitative, a typical flow-range for the coating of one medical device with a surface of 25 cm$^2$ in a reactor vessel will be 5 ml/min to 10 l/min for a reactor vessel with a volume of 0.5 to 2 l. Depending upon the desired conditions it is possible to use for example a piston pump, a lobe pump, a diaphragm or membrane pump, a rotary pump, a peristaltic pump, or any other pump that meets the requirements. Examples of suitable pumps are rotary lobe pumps (max. pressure of 6 bar for a flow of up to 6–7 l/min) and diaphragm pumpa (up to 40 bars) for a flow of up to 10 L/min). In some embodiments the pumps may be capable to reverse the flow direction, which could be useful e.g. in case of clogging of the channels, or to clean membranes.

Particularly, if the set-up comprises more than one container for solutions for passing through the reactor vessel, it may comprise one or more fluid selectors, e.g. solenoid valves, to switch from one solution to another during the different steps of the coating process. The dead volume between fluid selector and reactor vessel will preferably be as low as possible. It is possible to use several inlets for different solutions. In a preferred embodiment solutions enter the reactor vessel via one inlet, for economic and practical reasons.

If the set-up comprises more than one container for solutions that can pass through the reactor vessel and one or more solutions from said container are to be recirculated, the set-up will also comprise at least one fluid selector at the outlet of the reactor vessel, in order to avoid contamination of one container for solutions with a another solution. It is preferred that a set-up for coating with recirculation facilities, still has a waste channel available. This allows excluding certain fractions of fluids that leave the set-up from recirculation. This can for example be advantageous for certain cleaning steps and also in some embodiments of the invention, when changing from one type of solution, e.g. coating solution, to another solution, e.g. acidic solution to decalcify a coating on the medical device.

A container for solution (12), used in a set-up according to the invention, is typically a sterilizable reservoir, made of an inert material with sealable entries for the channels through which solutions, such as coating solution, acidic solution and cleaning solutions as described above, can be transported to (and optionally from) the reactor vessel. In particular in an embodiment without recirculation the solution will preferably be taken from the lower half of the container (12), e.g. via an outlet at that level or via a pipe or tube stuck in the reservoir with the opening at that level (15). In an embodiment with recirculation-facility, the inlet from which the recirculated solution enters the container, may be placed anywhere in the container. Preferably it is placed relatively far apart from the outlet of the container, preferably near or at the top of the container (16).

The size of a container for coating solution may vary depending upon the medical device to be coated. A typical minimum required size for a container for the coating solution to deposit a coating of 25 to 40 μm on a medical device with a surface of 25 cm$^2$ is about 1 l. The container may be insulated in a manner known in the art. In a preferred embodiment the container is double-jacketed. The container may further comprise a system for stirring or agitating the solution (7), contained inside it. Suitable means for stirring or agitating are those typically used by the skilled professional, such as a magnetic stirring system. The container may also comprise a device for maintaining a constant temperature of the solution held inside. The device for controlling the temperature (18) can be present instead of or in addition to a separate device for maintaining a constant temperature, present in or at the reactor vessel. A channel may also be thermostated, e.g. by letting part of the channel pass through a cryostate, by wrapping a heating-mantle around part of the channel or by passing part of the channel over a peltier element. A channel may also be insulated.

Several medical devices can be coated according to a method of the present invention in one batch. This can be achieved by placing more than one medical device in a single reactor vessel, but also by using more than one reactor vessel. These reactor vessels, each of which can comprise one or more medical devices, can be placed in parallel or in series of one another. It is preferred to place these reactor vessels in parallel, which makes it possible that through each reactor vessel a solution having the same composition, having the same pH, is flown. There is no particular limit to the number of reactor vessels, although the dimensions of the entire set-up and the capacity of the pump or pumps may have to be adjusted. In a preferred embodiment, the number of reactor vessels in a reactor according to the invention is between one and ten. Reactors comprising multiple reactor vessels may contain the same or different bioactive agents to be incorporated into a coating applied onto a medical device by a method according to the invention.

Figure 3:
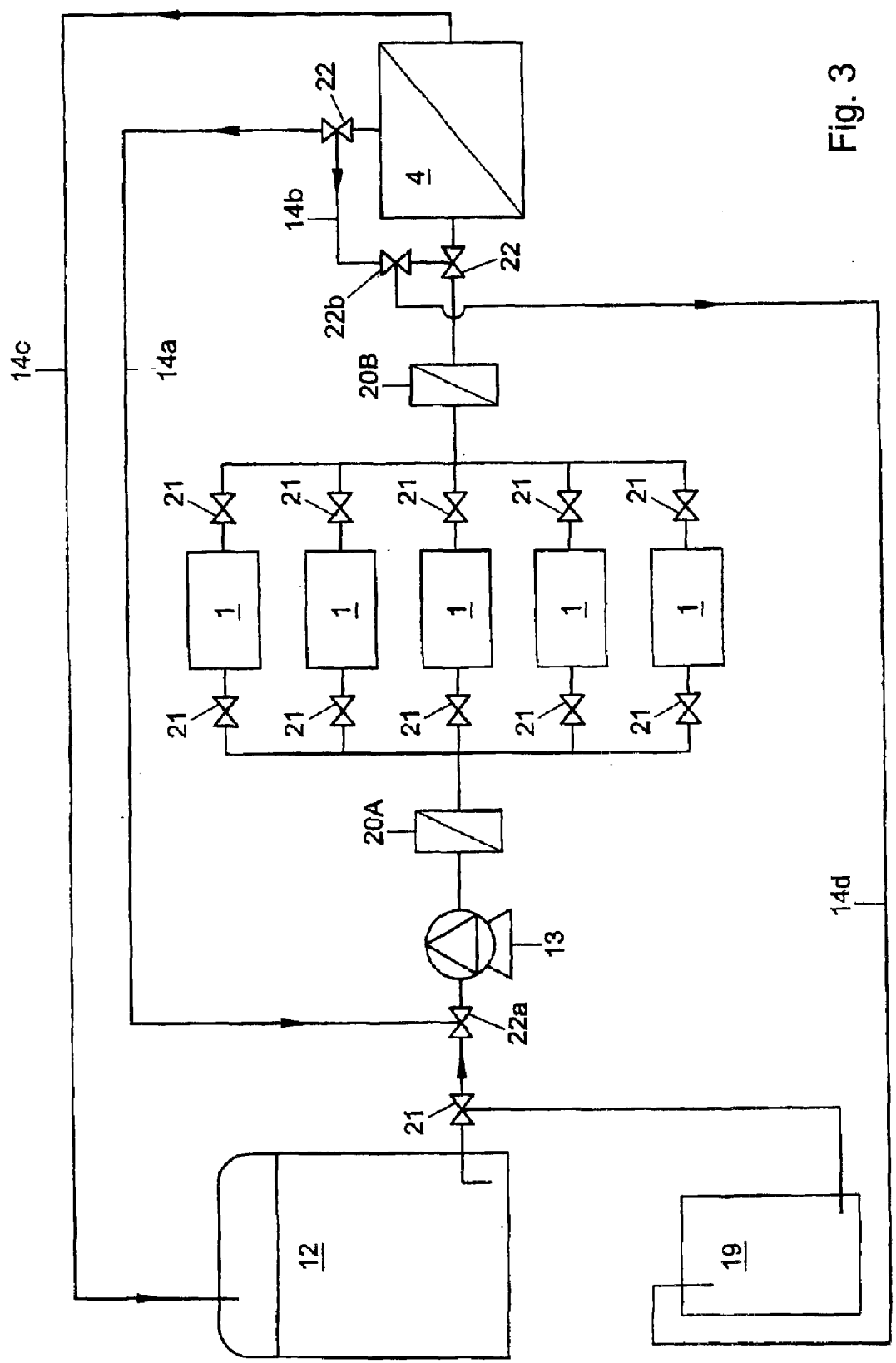
FIG. 3 depicts a schematic illustration of a reactor having several reactor vessels in parallel.

An example of a preferred reactor with several reactor-vessels in parallel is shown in FIG. 3. In this embodiment, bioactive agent can be lead from a container (19) to the reactor vessels (1) which may hold implants. The container (19) is preferably thermostated, e.g. at 37° C. The required volume depends upon the application. For may applications a volume of 5–20 l will suffice. The reactor comprises several valves ((21) and (22)). Thus one pump (13) can be employed to transport either bioactive agent from container (19) or calcifying solution from container (12) via filter (20a) (e.g. an antimicrobial 0.2 μm filter) to the reactor vessels. By closing a valve (21) at the inlet side of a reactor vessel, a reactor vessel can (temporarily) be excluded from the fluid-flow.

The outlets of the reactor vessels are joined and the fluid leaving the reactor vessels passes a second filter (20b), before the fluid enters a partition (4). A tangential flow filter has been found to be a very suitable partition. The tangential filter is equipped with a suitable membrane, e.g. a membrane with a molecular cut-off of 10,000 g/mol and/or a filter surface of 1–4 m$^2$. The partition splits the fluid in a fraction containing the bioactive agent and a fraction that mainly comprises calcifying ingredients (calcium, phosphate and other inorganic ions). The latter fraction may optionally be pumped back to the calcifying solution container (12), and may be re-used. The fraction containing the bioactive agent can be returned to the container (19) (not shown) or—in a preferred embodiment—it can be lead back to the reactor vessels via channel (14a) into valve (22a), where it may be mixed with a (dosed) quantity of calcifying solution from container (12), before being pumped into the reactor vessel again. Optionally the fraction containing the bioactive agent may be passed over the partition (4) more than once, via channel (14b). This may for example be useful for recovering the bioactive agent at the end of a coating process. The bioactive agent may thus be concentrated before being returned to container (19) via channel (14d) or to another storage facility (not shown).

In one embodiment of the present invention, after being coated with a method according to the invention as described above, a medical device may further be treated with an acidic solution in order to redissolve inorganic material of the coating, whilst the bioactive agents remain deposited on the medical device. This process can be performed in a reactor vessel according to the invention, a bioreactor such as described in European Patent Application 98203085.0 or in reactors, typically known from the state of the art. Such a treatment with acidic solution is particularly suitable for medical devices coated according to a method of the invention, wherein the coating comprises a bioactive agent and a ceramic material such as a calcium phosphate. In this case such a process may be referred to as a decalcification process and is preferably performed in an acidic solution with a pH in the range of 2–5 (measured at 25° C.). The temperature during the redissolving process is typically in the same range as the coating process. The temperature may be adjusted to (selectively) improve solubility of inorganic ions. A decalcification treatment is in particular applicable to a coated medical device, of which the coating comprises peptidic compounds or other bioactive agents that do not readily redissolve during such treatment.

Surprisingly it has been found that on medical implants coated according to the present invention, wherein a suitable growth factor has been incorporated, nucleation and growth of calcium phosphate crystals is induced, both in vitro and in vivo. Both coatings on medical devices wherein inorganic ions, such as calcium and phosphate have been redissolved and coatings wherein the inorganic ions have not been redissolved, have been found to act as a type of template or matrix for mineralization. This advantageous property allows the application of medical devices to serve as a scaffold for tissue engineering bone tissue.

Furthermore, said property of course also increases the suitability of a medical implant for the purpose it originally had, i.e. being implanted in a patient in need of a bone substitute. The coating described herein can induce deposition of a variety of calcium phosphate compounds containing carbonate and others ions on the surface of an implantable device. The layers will be similar in composition and crystallinity to bone and teeth minerals and have desired bioresorbability, bone-bonding properties to improve the biological fixation of medical devices to living calcified tissue.

A calcium phosphate coating obtained by a method according to the invention may further form a composite with calcium phosphate crystals, for instance in vivo, leading to a biomimetic coating with mechanical properties superior to those of conventional ceramic coatings, in par ticular if certain proteins have been incorporated in the coating, by employing a method according to the invention. It is believed that such a protein may function as a reinforcement of a biomimetic coating by bonding calcium phosphate crystals together. Such reinforcement effect may exist for coatings that have been decalcified or not. Examples of such proteins are albumin, casein, gelatin, lysosime, fibronectin, fibrin, chitosan, polylysine, polyalanine, polycysteine.

Furthermore, the coating may enhance attachment of cells and improve the biocompatibility and bone-bonding properties of medical devices such as medical implants.

This invention is illustrated by the following examples but should not be construed to be limited thereto. In the examples, the percentages are expressed in weight unless specified otherwise.

EXAMPLE 1

1.1 Preparation of a medical device prior to coating

Pieces of titanium alloy are cut from a sheet of commercially available $Ti_6Al_4V$ foil or rods. $Ti_6Al_4V$ plates of 10×10×2 mm and cylinders of 5 mm in diameter and 10 mm in length are used. Pieces and wires will be referred to as implants hereafter. Furthermore $Ti_6Al_4V$ wires of 1 mm in diameter are used. Prior to coating, the implants are sand- or grit-blasted to increase their surface roughness. The implants are ultrasonically cleaned for 15 min in acetone, then ethanol (70%) and finally pure water. The $Ti_6Al_4V$ plates are then etched for 30 min in an ultrasonic cleaner with a concentrated acid mixture containing distilled water, hydrochloric acid (HCl, 36%) and sulfuric acid ($H_2SO_4$, 96%) with a volume fraction of 2:1:1. A soft etching procedure can be alternately applied by soaking the implants into a mixture made of 994 ml of pure water, 2 ml of hydrofluoric acid (HF, 40%) and 4 ml of nitric acid ($HNO_3$, 50%). The etched $Ti_6Al_4V$ implants were thoroughly washed with pure water. After etching and rinsing, all samples are placed into a 3 liters insulated bioreactor and sterilized with steam at 121° C. for 30 minutes. Directly before placement in the reactor vessel the implant is cleaned with acetone, ethanol and water respectively.

1.2 Preparation of a thin amorphous calcium phosphate coating.

A reactor vessel equipped with a magnetic bar is filled with 800 ml of distilled water. A thermocouple is placed into the solution and the solution is heated at 37° C. by a heating element. All inorganic salts are precisely weighed as indicated in Table 1 and NaCl, $MgCl_2.6H_2O$) and $CaCl_2.2H_2O$ are dissolved in this in 800 ml of distilled water, with stirring.

TABLE 1

| chemicals for pre-coat solution (5 × SBF) | |
|---|---|
| Compound | Amount (g) |
| NaCl | 40.0 ± 0.1 |
| $MgCl_2$, $6H_2O$ | 1.52 ± 0.01 |
| $CaCl_2$, $2H_2O$ | 1.84 ± 0.01 |
| $Na_2HPO_4$,$2H_2O$ | 0.89 ± 0.01 |
| $NaHCO_3$ | 1.76 ± 0.01 |

A tube with flowing $CO_2$ gas is plunged into the reactor vessel and $CO_2$ is bubbled through the solution for 10 minutes. The sodium bicarbonate is added to the reactor vessel and dissolved with stirring and $CO_2$ bubbling. This is followed by adding sodium hydrogen phosphate which is also dissolved during stirring. Next distilled water is added to a final volume of 1000 ml. This pre-coat solution is also known as 5×SBF (5×simulated body fluid).

After dissolving all the salts, the $CO_2$ plunge is removed and the implants are submerged into the solution. The solution is stirred at 300 rpm and the temperature is kept constant at 37° C. The implants are removed after 24 hours and dried in open air. These "pre-coated" implants are autoclaved at 121° C. for 30 min and placed into a sterile cartridge for coating with the coating solution containing a growth factor.

1.3 Preparation of a 35 μm thick, more crystalline calcium phosphate coating.

The coating solution is prepared as follows to provide a "metastable solution". The chemicals are weighed separately in a 50 ml polystyrene vial as indicated in Table 2.

TABLE 2 chemicals for coating solution

| Compound | Amount |
|---|---|
| NaCl | 8.0 g |
| HEPES | 11.92 g |
| $MgCl_2.6H_2O$ | 0.01 g |
| $CaCl_2.2H_2O$ | 0.59 g |
| $Na_2HPO_4.2H_2O$ | 0.36 g |
| $NaHCO_3$ | 0.08 g |

800 ml demineralized water is poured into an Erlenmeyer flask and a magnetic bar is added. The chemicals are added to the Erlenmeyer flask and dissolved by stirring. The sequence of adding the chemicals is: NaCl, HEPES, $MgCl_2.6H_2O$, $CaCl_2.2H_2O$, $Na_2HPO_4.2H_2O$, $NaHCO_3$ The pH with is adjusted drop wise with 2 M NaOH to 7.40±0.05 at room temperature. The solution is poured into a 1000 ml volumetric flask and distilled water is added to 1000 ml precisely. The solution is filtered through a 0.2 μm membrane filter under vacuum into a 1000 ml thick-walled glass storage bottle, It is verified that no precipitation or flakes are detected in the solution. Next the solution is filtrated into a sterilized 1000 ml glass bottle through a 0.2 μm top bottle filter under sterile conditions. The bottle is sealed aseptically. This solution is transferred to a container, such as schematically drawn in FIG. 2, and the solution is stirred at 150 rpm.

Solutions of bonemorphogenetic proteins (BMP) in metastable solution are made to concentrations of 1, 5 and 10 mg/ml.

The used reactor vessel is a cartridge-like object with a volume of approximately 1 l. A Pellicon Millipore Biomax 10, cut off 10 kDa. Polyethersulfone, low protein binding affinity is placed at the outlet. A Millipore Opticap 0.2 μm filter is placed at the inlet. The pre-coated implants (prepared as mentioned above) are placed in the reactor vessel and the reactor vessel is filled with coating solution further comprising BMP in a concentration as indicated above. The solution is heated to 37° C. and the temperature is then kept constant. The cartridge is sealed and a piston pump is used to generate a flow of 10 ml metastable solution per minute is pumped from the container through the cartridge and recirculated to the container.

After a calcium phosphate coating of 25 to 40 μm thickness has been deposited on the implant, the process is stopped. The thickness is monitored by conductivity measurement using a specially designed conductivity meter containing two metal plate electrodes in parallel, which is placed inside the reactor, the decrease in conductivity between both electrodes is found to be a good measure for the thickness of the coating on the plates. 1 liter of metastable solution can produce a coating of 25 to 40 μm on medical devices having a surface to be coated of 25 cm 2.

EXAMPLE 2

Conditions for this example were similar to Example 1 unless stated otherwise.

After coating one side of 2×2 cm Ti6Al4V plates with a thin (2±1 μm) amorphous calcium phosphate coating, according to the procedure given in Example 1, a second layer of carbonated hydroxyapatite (CHA) coating further comprising a growth factor was applied on top of the first layer. This was achieved by using a supersaturated calcium phosphate (CPS) solution to which 5 mg/l of bone morphogenetic protein (rhBMP-2, Genetic Institute) had been added (For other components: see Example 1). After immersion for 24 hours in this CPS solution at 37° C., the coated plates were thoroughly rinsed in demineralized water and dried at 50° C. for 2 hours. A crystalline and thick CHA layer was evenly deposited on the Ti6Al4V plates.

The coating had an average thickness of 50±10 μm (thickness gauge from Radiometer, minitest 2100). The dissolution of CHA coating was measured using a calcium ion selective electrode (ISE) with a calomel reference connected to a potentiometer (Metrohm). A one-side coated-Ti6Al4V plate (2×2 cm) was immersed into 10 ml of saline solution (NaCl 8 g/l) buffered at pH 7.3 with trisaminoethane and hydrochloric acid and thermostated at 37° C. The dissolution of coating was monitored by the calcium concentration released in this saline solution. Simultaneously, aliquots of 100 μl of medium were taken for measuring the protein content with a micro BCA kit (Sigma). The release of growth factor was expressed as a percentage of total amount incorporated into the CHA coating. The total growth factor content was determined by complete dissolution of CHA coating in 5 ml of hydrochloric acid solution (1 M) and then by using the previously described protein assay.

The results of the dissolution tests are shown in FIGS. 4 (calcium) and 5 (growth factor).

EXAMPLE 3

Calcium phosphate coatings containing an antibiotic (tobramycin) were produced onto titanium alloy (Ti6Al4V) implants using a biomimetic approach. Thin and amorphous calcium phosphate (ACP) coatings were deposited onto Ti6Al4V plates by immersion in 5 times concentrated simulated body fluid (SBF) for 24 hours at 37° C. After cleaning, the Ti6Al4V plates or discs were immersed in a 5 times concentrated simulated body fluid (SBF×5) (24, 25). This SBF×5 solution contained NaCl (733 mM), $CaCl_2.2H_2O$ (12.5 mM), $MgCl_2.6H_2O$ (7.5 mM), $Na_2HPO_4.2H_2O$ (5.0 mM) and $NaHCO_3$ (21.0 mM). Salts were dissolved in. 1000 ml of demineralised water by bubbling through carbon dioxide gas at a flow of 650 ml/min and constant stirring for 10 min. After complete dissolution of salts, the carbon dioxide gas supply was removed and pH of solution was approximately 6.0. The Ti6Al4V samples were immersed in the SBF×5 solution at 37° C. for 24 hours under constant stirring at 200 rpm. Over immersion time, carbon dioxide gas was exchanged by air leading to an increase of pH and sursaturation in the SBF×5 solution. At a pH of 6.8, calcium phosphate precipitated in solution and simultaneously onto the Ti6Al4V plates. After 24 hours, the pH reached approximately 8.0 due to the buffering capacity of phosphate and carbonate ions contained in the SBF×5 solution. Then, samples were ultrasonically rinsed in demineralised water and dried overnight at room temperature. A thin and amorphous calcium phosphate (ACP) layer covered evenly the substrate. The ACP-coated implants were steam sterilized at 121° C. for 30 min.

Then, the ACP-coated Ti6Al4V samples were immersed in another calcium phosphate supersaturated (CPS) solution under aseptic conditions in within a small volume (i.e. 25–50 ml) to minimize the quantity of drug Tobramycin. The CPS solution containing NaCl (146 mM), $CaCl_2.2H_2O$ (4 mM), $MgCl_2.2H_2O$ (0.05 mM), $Na_2HPO_4.2H_2O$ (2 mM), $NaHCO_3$ (1 mM) and buffered at pH 7.4 with 50 mM N-[2-hydroxyethyl] piperazine-N'-[2-ethanesulfonic acid] (HEPES) and NaOH (2 M). Increasing quantities of Tobramycin of 0, 100, 200 400, 600 or 800 mg/l were dissolved into the CPS solution. After 48 hours at 37° C. and under constant stirring at 100 rpm, the Ti6Al4V samples were uniformly covered with a white, crystalline and thick carbonated hydroxyapatite (CHA) layer. The CHA-coated samples were washed with demineralised water afterwards and dried overnight in open air, then kept in plastic containers at room temperature. When tobramycin was incorporated, the samples were stored in a refrigerator at 4° C.

The uniformity of coatings was controlled macroscopically. The coverage of Ti6Al4V substrate was estimated as a percentage of white-covered surface over the total surface. The coating thickness was measured by magneto-induction using an Eddy-current probe (Electro Physik, Minitest 2100, Radiometer, Zoetermeer, The Netherlands). The thickness meter was calibrated by using polyethylene foils of 10, 50 and 100 μm on Ti6Al4V plates. A minimum of 10 thickness measurements was performed for each coated sample. Scanning electron microscopy (Philips ESEM-FEG XL 30, Eindhoven, The Netherlands) was used to study coating morphology. The coatings were characterized by infrared spectroscopy (FTIR, Perkin Elmer, Spectrum 1000, Breda, The Netherlands). About 1.2 mg of coating sample was scraped off and mixed with 300 mg of KBr. A transparent pellet was made in a 13-mm mold with a pressure of 10 tons. FTIR spectra were recorded in the 400—400 $cm^1$ range with 2 $cm^{-1}$ resolution using 16 scans and background substraction. XRD patterns were recorded in the 5–60 degree/2θ range with an X-ray diffractometer XG 30 kV (Miniflex 2005C101, Rigaku, Tokyo, Japan) using a Cu Kα radiation.

The tobramycin content was determined using an automated fluorescent polarising immunoassay (FPIA, FLx, Abbott Diagnostics, Hoofddorp, The Netherlands). The minimal detectable concentration of tobramycin in solution was 0.05 μg/ml. The amount of antibiotic incorporated into the coatings was measured as following. The coated plates were dried in an oven for 60 minutes at 50° C., cooled off in a desiccator and weighted precisely. When this process was repeated, no further weight loss could be measured. Then, the coatings were scraped off from the Ti6Al4V substrate using a razor blade, weighted and dissolved in 1 ml of HCl (0.5 M). The FLx instrument was calibrated using 0, 0.5, 1.5, 3.0, 6.0, 10.0 μg/ml standards (Abbot Diagnostics). Controls of 1, 4 and 8 μg/ml tobramycin were measured together with each sample run. The quantity of tobramycin in the coating was expressed in μg/mg. A minimal concentration of 0.001 μg/mg tobramycin could be detected in the coating.

A carbonated hydroxyapatite (CHA) layer of approximately 40 microns in thickness was formed. About 3 μg/mg of tobramycin were co-precipitated with the CHA crystals onto titanium alloy plates (FIG. 7). The dissolution of coating and release of tobramycin were also measured in vitro using saline solution buffered at pH 5.0 or 7.3 at 37° C.

Bacterial inhibition

Culture Agar medium (Mueller-Hinton) was dissolved in demineralized water and sterilized by autoclaving at 121° C. for 20 minutes. The hot Agar solution was poured into culture dishes of 10 cm in diameter and cooled to room temperature under sterile conditions. A suspension of *Staphylococcus aureus* bacteria (Type ATCC 12600) was added to a bouillon made of CASO in sterile water and incubated for 2 hours at 35° C. in a shaking water bath. Then, 0.5 ml of this bouillon was sprayed over the total area of each culture dish. A sterile Ti6Al4V disc, 10 mm in diameter, was directly placed in the center of each culture dish with the coating facing the Agar medium. A Ti6Al4V disc coated with the biomimetic calcium phosphate coating, but without antibiotic was used as negative control. A cellulose filter disc (10 mm in diameter) impregnated with Y 10 μl of 750 mg/l tobramycin solution and placed on the culture dish was used as positive control. Biomimetically coated titanium alloy discs incorporating various amount of tobramycin were placed in the same manner. Finally, the Agar culture dishes with samples were incubated for 24 hours at 37° C. The inhibition zones of bacterial growth that formed around the discs were measured in millimeters. Tobramycin released out of the biomimetic coated plates could inhibit growth of *Staphylococcus aureus* bacteria (FIG. 9). The biomimetic CHA coatings containing antibiotics can be used to prevent post-surgical infections in orthopaedic or trauma.

EXAMPLE 4

(comparative)

Plasma sprayed Hydroxyapatite coatings on 2×2 cm titanium alloy (Ti6Al4V) plates were immersed into a solution containing NaCl (146 mM), $CaCl_2.2H_2O$ (2 mM), $Na_2HPO_4.2H_2O$ (0.8 mM), buffered at pH 7.4 with 50 mM HEPES and NaOH (2 M), with the addition of 100, 200, 400 or 1000 mg/l of tobramycin. The plasma sprayed calcium phosphate coating was stable in this under-saturated solution showing neither weight loss due to dissolution nor weight increase due to reprecipitation as well as no morphological change. The plasma sprayed calcium phosphate coated plates were immersed in 50 ml of these solutions for 10, 40 minutes and 48 hours in a shaking water bath at 37° C. After soaking for different time periods the plates were washed with water, dried overnight at room temperature and finally stored in a closed vial at 4° C. prior-to tobramycin measurements. A maximum of about 0.3 μg/mg of Tobramycin, so 10 times lower than for the biomimetic coprecipitation, could be adsorbed onto the plasma sprayed hydroxyaptite coating (FIG. 8).

Therefore, this comparative shows that a preformed coating like the plasma sprayed Hydroxyapatite coating cannot incorporate sufficient amount of antiobiotic by simply soaking in tobramycin solutions. The antibiotic is just superficially adsorbed and thereby release within seconds or washed away by body fluids during implantation. This soaking experiment of preformed coating into tobramycin solution illustrates that this burst release will not be sufficient to prevent-post surgical infections. It is therefore essential for a successful antibiotic coated implant to be processed according to the present invention as delineated in example 3.

EXAMPLE 5

20 NZW rabbits were used in an experiment to determine the effectiveness of the release of tobramycin from the biomimetic apatite coating. All 20 rabbits were operated by drilling a hole into the left tibia from the knee cap into the bone marrow shaft. Then 100 μl of $10^6$ *Staphylococcus aureus* bacteria were injected into the drilling hole. From the 20 rabbits, 10 received a titanium alloy cylinder, coated with CHA coating containing tobramycin and another 10 coated but without tobramycin. After implantation for 4 weeks, the tibia was explanted and the posterial half of the tibia was used for histology/histomorphometry and the anterior half was used for microbiology.

The anterior half was ground in a mortar and homogenized in PBS solution. Dilutions in 10 fold were plated on a blood agar plate and the total CFU was counted after incubated for 24 hours at 37° C. Results of microbiology colony forming units are shown in FIG. 10. In 9 of 10 HA treated animals as compared to 3 of 10 Tobra-HA treated animals, bacteria were found in the local implant bed (p=0.019). More bacteria were retrieved from the HA coated implants as compared to the trobramycin containing implants (p=0.015). This results indicated that infections was annihilated post-surgically in 70% of the case despite the extremely high dose of CFU injected during surgery. This study clearly demonstrates a prophylactic effect of a tobramycin containing hydroxyapatite coating against the development of a prosthetic infection since more bacteria were retrieved from HA coated Ti implants as compared to Tobramycin-HA coated Ti implants. This has a potential clinical relevance for the prevention of periprosthetic infections in high-risk patients that receive a non-cemeted total joint prosthesis.

What is claimed is:

1. A method for coating a medical device comprising:
   providing a reactor having at least one partition that retains a bioactive agent in the reactor;
   placing the medical device in the reactor;
   contacting the medical device in the reactor with a solution including inorganic ions;
   depositing inorganic ions on the medical device;
   passing the solution including non-deposited inorganic ions through the at least one partition;
   contacting the medical device in the reactor with a bioactive agent; and
   retaining the bioactive agent in the reactor such that the bioactive agent is deposited on the device.

2. A method according to claim 1 wherein said inorganic ions are selected from the group consisting of calcium ions, magnesium ions, sodium ions, phosphate ions, carbonate ions, chloride ions and hydroxide ions.

3. A method according to claim 1, wherein said partition has a low permeability towards said bioactive agent and a high permeability towards said coating solution.

4. A method according to claim 3, wherein said partition is a molecular weight cut-off membrane.

5. A method according to claim 1, wherein said medical device has been coated with an initial layer of inorganic material.

6. A method according to claim 1, wherein after coating the medical device, said medical device is contacted with an acidic aqueous solution to redissolve inorganic salts of the coating and to obtain a coating of bioactive agent.

7. A method according to claim 1, wherein said coating solution comprises one or more of 0.5 to 10 mM calcium ions, 0.5 to 6 mM phosphate ions, 0 to 1 mM magnesium ions, 0 to 0.5 mM sodium ions, 0 to 0.5 mM chloride ions, 0 to 5 mM carbonates and N-2-hydroxyethylpiperazine-N'-4-ethane sulfonic acid and/or tris(hydroxymethyl) aminomethane in a total concentration between 0 and 100 mM.

8. A method according to claim 1, wherein the medical device is a metallic, organic, polymeric, or ceramic medical implant.

9. A method according to claim 1, wherein said bioactive agent is a peptide, a polypeptide, a protein or a combination thereof.

10. A method according to claim 1, wherein said bioactive agent is an antibiotic agent, a growth factor or growth hormone, a bone reinforcing protein, a cell adhesion factor, autologous serum, a vitamin or a combination of said compounds.

11. A method according to claim 9, wherein said bioactive agent is selected from the group consisting of tobramycin, vancomycin, albumin, casein, gelatin, lysosime, fibronectin, fibrin, chitosan, polylysine, polyalanine, polycysteine, Bone Morphogenetic Protein (BMP), Epidermal Growth Factor (EGF), Fibroblast Growth Factor (bFGF), Nerve Growth Factor (NGF), Bone Derived Growth Factor (BDGF), Transforming Growth Factor-β1 (TGF-β1), Transforming Growth Factor-β (TGF-β), the tri-peptide arginine-glycine-aspartic acid (RGD), vitamin D3, dexamethasone, and human Growth Hormone (hGH) or a combination of said compounds.

12. A method according to claim 1, wherein said bioactive agent is present in the reactor vessel in an initial concentration of 0.01 to 10,000 mg/l.

* * * * *